United States Patent
Nikolic et al.

(10) Patent No.: US 8,454,833 B2
(45) Date of Patent: Jun. 4, 2013

(54) COUNTER-PRESSURE FILTRATION OF PROTEINS

(75) Inventors: Nebojsa Nikolic, Vienna (AT); Michaela Frey, Klosterneuburg (AT); Wolfgang Grabmayer, Vienna (AT); Thomas Jancik, Vienna (AT); Matthias Fried, Limberg (AT); Klaus Tschetschkowitsch, Vienna (AT); Kurt Schnecker, Vienna (AT); Barbara Riegler, Vienna (AT); Alma Kasapovic, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

(21) Appl. No.: 13/297,587

(22) Filed: Nov. 16, 2011

(65) Prior Publication Data
US 2012/0136139 A1    May 31, 2012

Related U.S. Application Data

(63) Continuation of application No. 12/860,411, filed on Aug. 20, 2010, now Pat. No. 8,075,781, and a continuation of application No. 12/860,424, filed on Aug. 20, 2010, now Pat. No. 8,075,782, which is a continuation of application No. 12/341,733, filed on Dec. 22, 2008, now Pat. No. 7,959,809, said application No. 12/860,411 is a continuation of application No. 12/341,733.

(60) Provisional application No. 61/017,418, filed on Dec. 28, 2007.

(51) Int. Cl.
*B01D 61/00* (2006.01)
*B01D 11/00* (2006.01)
*C02F 1/44* (2006.01)
*A61K 35/14* (2006.01)

(52) U.S. Cl.
USPC ............ 210/651; 210/650; 210/645; 210/90; 435/2; 530/383; 530/384

(58) Field of Classification Search
USPC ................ 210/645, 90, 659, 651, 560; 435/2, 435/220.27; 530/383, 380, 384, 414
See application file for complete search history.

(56) References Cited

U.S. PATENT DOCUMENTS

| 4,141,887 A | 2/1979 | Seufert |
| 4,774,323 A | 9/1988 | Newman et al. |

(Continued)

FOREIGN PATENT DOCUMENTS

| EP | 1037923 B1 | 9/2000 |
| WO | WO-2005/040214 A1 | 5/2005 |

OTHER PUBLICATIONS

Examination Report for Singapore Patent Application No. 201004546-6, Received Oct. 1, 2012.

(Continued)

*Primary Examiner* — Ana Fortuna
(74) *Attorney, Agent, or Firm* — Marshall, Gerstein & Borun LLP

(57) ABSTRACT

A method is disclosed for filtering a protein in a liquid mixture in a manner that does not substantially damage or otherwise limit the recovery of the protein in the filtration filtrate. The method generally includes passing a liquid mixture containing a protein (e.g., an aqueous vWF mixture) through a filter while applying a counter pressure to the liquid mixture filtrate to accurately reduce and control the pressure differential across the filter. The disclosed method has the advantage that relatively high filtration flow rates can be achieved at relatively low pressure differentials, in contrast to high pressure differentials, which actually reduce the filtration flow rate of protein liquid mixtures. Further, the method can recover substantially all of the protein that is initially present in the liquid mixture.

23 Claims, 2 Drawing Sheets

U.S. PATENT DOCUMENTS

| | | | |
|---|---|---|---|
| 4,800,808 A * | 1/1989 | Lidman | 99/453 |
| 5,470,954 A | 11/1995 | Neslund et al. | |
| 5,728,549 A * | 3/1998 | Liersch et al. | 435/69.2 |
| 5,888,401 A | 3/1999 | Nguyen | |
| 6,193,891 B1 | 2/2001 | Kent et al. | |
| 6,228,613 B1 | 5/2001 | Fischer et al. | |
| 6,485,762 B1 | 11/2002 | Rizvi et al. | |
| 6,579,723 B1 | 6/2003 | Mitterer et al. | |
| 6,808,638 B1 | 10/2004 | Purdum | |
| 6,967,239 B1 | 11/2005 | Chtourou et al. | |
| 7,439,013 B2 | 10/2008 | Kuno et al. | |
| 7,785,594 B2 * | 8/2010 | Saint-Remy et al. | 424/145.1 |
| 7,932,355 B2 | 4/2011 | Chtourou et al. | |
| 7,959,809 B2 * | 6/2011 | Nikolic et al. | 210/651 |
| 8,075,781 B2 * | 12/2011 | Nikolic et al. | 210/651 |
| 2004/0005310 A1 * | 1/2004 | Rapp et al. | 424/94.63 |
| 2009/0123989 A1 * | 5/2009 | Weggeman | 435/239 |

OTHER PUBLICATIONS

Truskey et al., "The Effect of Membrane Filtration Upon Protein Conformation," *J. Parenteral Science & Technology*, 41(6):180-93 (1987).

Letter to the Editor, *J. Parenteral Science & Tecnology*, vol. unknown, pp. 144-146 (ca. 1987) (discussing Truskey et al., "The Effect of Membrane Filtration Upon Protein Conformation," *J. Parenteral Science & Technology*, 41(6): 180-93 (1987)).

Bowen et al., "Properties of Microfiltration Membranes: The Effects of Adsorption and Shear on the Recovery of an Enzyme," *Biotechnology and Bioengineering*, 40:491-97 (1992).

"Filtration," *Kirk-Othmer Encyclopedia of Chem. Tech.*, 4$^{th}$ ed. 10:788-853 (1993).

Siediecki et al., "Shear-Dependent Changes in the Three-Dimensional Structure of Human von Willebrand Factor," *Blood*, 88(8):2939-50 (1996).

Singh et al., "Effects of Fluid Shear on the Conformation of Human von Willebrand Factor Studied by Neutron and Light Scattering," AICHE Annual Meeting paper dated Nov. 1996.

Pareti et al., "Proteolysis of von Willebrand Factor and Shear Stress-Induced Platelet Aggregation in Patients with Aortic Valve Stenosis," *Circulation*, 102:1290-95 (2000).

Technical Brief, "Protein Concentration and Diafiltration by Tangential Flow Filtration," Millipore Corporation, 25 pages (2003).

Mazurier et al., "In Vitro Study of a Triple-Secured von Willebrand Factor Concentrate," *Vox Sanguinis*, 86:100-04 (2004).

Schneider et al., "Shear-Induced Unfolding Triggers Adhesion of von Willebrand Factor Fibers," PNAS, 104(19):7899-903 (2007), available at www.pnas.org/cgi/doi/10.1073/pnas.0608422104.

Singh et al., "Fluid Shear Induces Conformation Change in Human Blood Protein von Willebrand Factor Solution Structure," AICHE Annual Meeting paper dated Nov. 2007.

International Search Report and Written Opinion for Application No. PCT/US2008/088005, dated Mar. 7, 2009.

Gésan et al., "Fouling during constant flux crossflow microfiltration of pretreated whey. Influence of transmembrane pressure gradient," *Journal of Membrane Science*, 80:131-145 (1993).

Mietton-Peuchot et al., "Use of gas-liquid porometry measurements for selection of microfiltration membranes," *Journal of Membrane Science*, 133:73-81 (1997).

Velasco et al., Protein fouling in microfiltration: Deposition mechanism as a function of pressure for different pH. *J. Colloid Interface Sci.*, 266: 148-52 (2003).

Gésan et al., Colmatage d'une membrane inorganique de microfiltration par du lactoserum. Recents *Progres en Genie des Procedes*, 5(15): 19-24 (1991).

Gésan-Guiziou et al., Critical stability conditions in skimmed milk crossflow microfiltration: Impact on operating modes. *Lait*, 80: 129-40 (2000).

Opposition to European Patent No. 2 242 479, Notice of Opposition, dated Jun. 27, 2012.

* cited by examiner

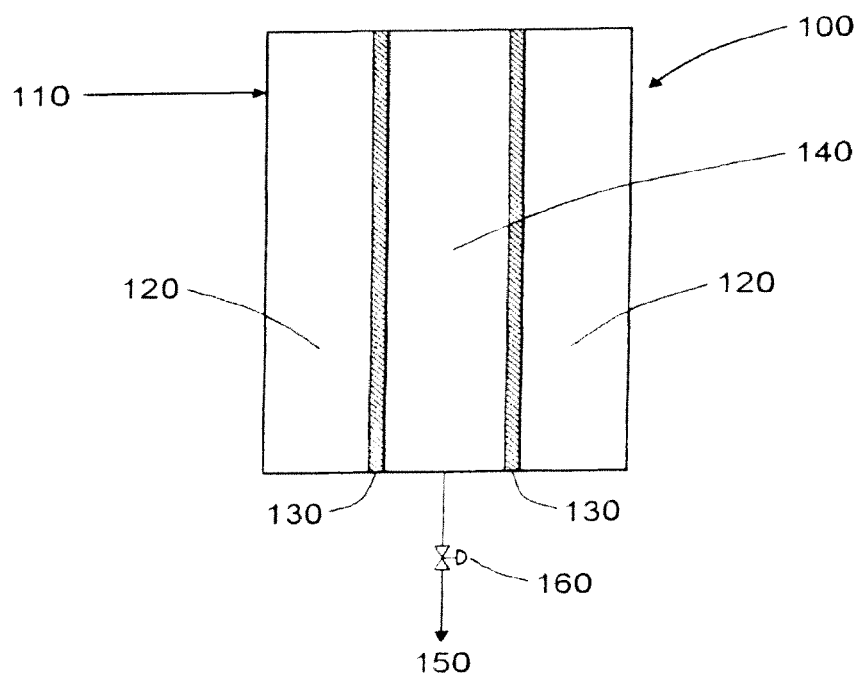

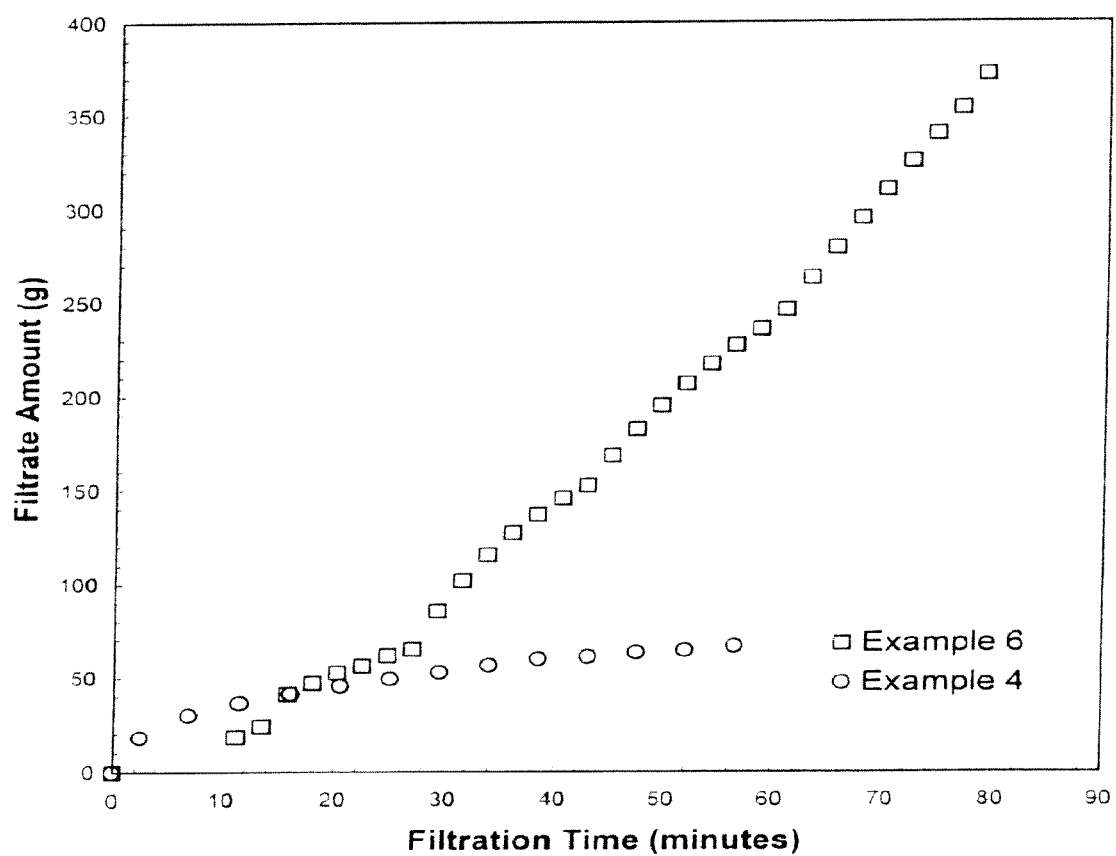

COUNTER-PRESSURE FILTRATION OF PROTEINS

CROSS-REFERENCE TO RELATED APPLICATIONS

This is a continuation of U.S. Ser. No. 12/860,411, now U.S. Pat. No. 8,075,781, and U.S. Ser. No. 12/860,424, now U.S. Pat. No. 8,075,782, both of which were filed on Aug. 20, 2010, and both of which are continuations of U.S. Ser. No. 12/341,733, now U.S. Pat. No. 7,959,809, filed on Dec. 22, 2008, which claims the benefit under 35 U.S.C. §119(e) of U.S. Ser. No. 61/017,418, filed on Dec. 28, 2007, the disclosures of which are incorporated herein by reference.

BACKGROUND

1. Field of the Disclosure

The disclosure relates generally to filtration methods for the purification of proteins. More particularly, the disclosure relates to the low-shear, counter-pressure sterile filtration of proteins susceptible to damage by shear forces (e.g., shear-sensitive proteins, blood coagulation cascade proteins), for example when being transported in a fluid.

2. Brief Description of Related Technology

Purified protein mixtures can be administered to patients for a variety of therapeutic uses. A purified protein mixture prepared for infusion into patients must be sterilized prior to use. A suitable sterilization process for some proteins includes membrane filtration of a purified protein mixture. The filter membrane can be sized to retain (i.e., remove from the protein mixture) particulates, microorganisms, and some viruses, while the proteins are able to pass through the membrane.

However, some proteins are not efficiently recovered as purified, sterilized proteins using conventional methods such as membrane filtration. This effect is most pronounced when attempting to filter proteins that are shear-sensitive and/or part of the blood coagulation cascade. An example of such a protein is the von Willebrand factor (vWF), which circulates in plasma complexed with factor VIII and assists in the regulation of biological blood coagulation activity. Specifically, the vWF proteins are sensitive to shear forces induced by the velocity gradient of a transporting fluid medium, in particular when the vWF proteins pass through or near a filter membrane (i.e., where flow constrictions and circuitous flow paths in the neighborhood of filter membrane pores result in particularly large velocity gradients). Thus, when filtration units are operated at sufficient pressures to ideally generate desirable process flow rates, increased flow rates (and the accompanying increase in induced shear forces) tend to reduce process yield, for example by damaging or destroying the proteins, and/or by reducing the filtration rate over time.

Accordingly, it would be desirable to develop a method of filtering a purified vWF mixture in a manner that does not substantially damage the vWF proteins, yet which method still permits a suitably high process throughput (i.e., filtration rate) over time. Additionally, it would be desirable to develop a filtering method generally applicable to any protein, such that the general protein can be filtered (e.g., sterile filtered) at an efficient rate without incurring substantial damage to/loss of the protein.

SUMMARY

The disclosed method is useful for filtering a protein in a liquid mixture in either a batch or continuous manner that does not substantially damage or otherwise limit the recovery of the protein in the filtration filtrate. The method generally applies a counter pressure to the filtrate to accurately reduce and control the pressure differential across a filter. The disclosed method has the advantage that relatively high filtration flow rates can be achieved at relatively low pressure differentials, in contrast to high pressure differentials which actually reduce the filtration flow rate of protein liquid mixtures. Further, the method can recover substantially all of the protein that is initially present in the liquid mixture.

More specifically, the disclosure provides a method of filtering a liquid protein mixture. According to one embodiment, the method includes providing a liquid mixture at a first pressure $P_1$ and passing the liquid mixture through a filter to form a filtrate at a second pressure $P_2$, and applying a counter pressure to the filtrate such that a pressure differential $P_1-P_2$ is not more than about 300 mbar. In another embodiment, the method includes the steps of providing a liquid mixture at a first pressure $P_1$, and passing the liquid mixture through a filter to form a filtrate at a second pressure $P_2$, and applying a counter pressure to the filtrate sufficient to yield an average flow rate of the filtrate of at least about 300 g/min·m² of filter surface area. The liquid mixture includes a carrier liquid, a protein at a first concentration $C_1$ relative to the carrier liquid, and a dispersed contaminant. The filtrate includes the carrier liquid and the protein at a second concentration $C_2$ relative to the carrier liquid. The filter is sized to remove at least a portion of the dispersed contaminant from the liquid mixture.

In yet another embodiment, the method is capable of filtering an aqueous protein mixture, and includes the steps of providing an aqueous mixture at a first pressure $P_1$, passing the aqueous mixture through a porous membrane filter to form a filtrate at a second pressure $P_2$, and applying a counter pressure to the filtrate such that a pressure differential $P_1-P_2$ is not more than about 90 mbar. The aqueous mixture includes water and vWF at a first concentration $C_1$ relative to the water. The filtrate includes water and the vWF at a second concentration $C_2$ relative to the water. The porous membrane filter includes pores sized from about 0.1 μm to about 0.5 μm.

In any of the above embodiments, the protein is preferably a shear-sensitive protein and/or a blood coagulation cascade protein. Further, the protein is preferably recovered in the filtrate such that a recovery ratio $C_2/C_1$ is at least about 0.95, more preferably at least about 0.99. Additionally, the pressure differential $P_1-P_2$ is preferably not more than about 90 mbar and the first pressure $P_1$ is preferably at least about 200 mbar gauge. Preferred embodiments of the above methods include those in which the carrier liquid is water, and/or the dispersed contaminant includes microorganisms. The protein can include von Willebrand Factor, Factor VIII, Factor XIII, and mixtures thereof. The filter preferably includes a porous membrane filter having pores sized from about 0.1 μm to about 0.5 μm, more preferably sized at about 0.2 μm or about 0.22 μm. Preferably, the filtrate product is substantially free of the dispersed contaminant.

Filtration of a protein under the application of counter-pressure allows the recovery the protein at high relative concentrations, high relative filtrate flow rates, and substantially constant filtrate flow rates that are not otherwise attainable in the absence of counter-pressure. This is in contrast to the general application of filter theory at least with respect to the filtrate flow rate, which predicts that the filtrate flow rate increases with increasing pressure differential across the filter (i.e., in the absence of counter-pressure).

Further aspects and advantages will be apparent to those of ordinary skill in the art from a review of the following detailed description, taken in conjunction with the drawing. While the compositions, films, and packets described herein are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWING

Two drawing figures are appended hereto to facilitate the understanding of the disclosure.

FIG. 1 is a cross-sectional view of an axisymmetric cartridge filter for use in the counter-pressure filtration of proteins.

FIG. 2 is a comparison of filtration rate data obtained using a conventional filtration method and a counter-pressure filtration method.

DETAILED DESCRIPTION

The method described herein is generally applicable to the filtration purification of a protein in a liquid mixture in a manner that does not substantially damage or otherwise limit the recovery of the protein during the filtration. In addition to the protein, the liquid mixture also includes a carrier liquid and a dispersed contaminant. The carrier liquid is the suspending medium for the protein and is not generally limited. A preferred carrier liquid is water. Similarly, the dispersed contaminant is not particularly limited and can include any dispersed solid material that is an undesirable component of the final, purified protein filtrate. In the case of a sterile filtration operation, the dispersed contaminant generally includes any of a variety of microorganisms (i.e., bacteria) that might be present in the liquid mixture.

The disclosed method is particularly preferably applied to the filtration of proteins that are shear-sensitive, part of the human blood coagulation cascade, or both (i.e., some suitable proteins, for example vWF, may be classified as both shear-sensitive and blood coagulation cascade proteins).

Shear-sensitive proteins that are suitable for purification using the disclosed counter-pressure filtration method include those that are susceptible to damage, destruction, loss of activity, and/or a reduction in filtration rate when transported as a suspension in a carrier liquid that is characterized by significant shear forces (i.e., relatively large velocity gradients). In general, a shear-sensitive protein is a protein which exhibits an inverse proportionality between filtration rate and applied shear (or applied pressure) above a critical applied shear (or applied pressure). The critical applied shear (or applied pressure) at which a transition between a directly proportional relationship for filtration rate and applied shear (or applied pressure) and an inversely proportional relationship (i.e., a transition occurring when the filtration rate is at a maximum) may be different for various shear-sensitive proteins. For example, critical applied shear can be at least about $2000 \text{ s}^{-1}$ (or at least about $4000 \text{ s}^{-1}$) and not more than about $8000 \text{ s}^{-1}$ (or not more than about $12000 \text{ s}^{-1}$). However, the qualitative behavior for different shear-sensitive proteins is expected to be similar. A shear-sensitive protein includes vWF, although the disclosed method is not particularly limited thereto. While vWF exists in plasma in a series of oligomeric/polymeric forms having molecular weights ranging from about 1,000 kDa (kilodalton) to about 20,000 kDa based on 520-kDa dimers, the disclosed method is not necessarily limited to a particular molecular weight range.

The disclosed method also is generally applicable to the purification of proteins in the human blood coagulation cascade (i.e., coagulation factors). For example, coagulation Factors II (about 37 kDa molecular weight), VII (about 50 kDa), VIII:C (about 260 kDa), IX (about 55 kDa to about 70 kDa), X (about 100 kDa), XIII (about 350 kDa), vWF (discussed above), and combinations thereof, some of which also are shear-sensitive, can be efficiently filtered and recovered using counter pressure.

Some particularly preferred purified proteins include single proteins such as Factors XIII or vWF and multi-protein combinations such as a Factor VIII:C/vWF complex. A preferred protein mixture that is not particularly shear-sensitive, but which is still favorably filtered using counter pressure, is a FEIBA VH mixture ("factor eight inhibitor bypassing activity (vapor heated)," available from Baxter, Deerfield, Ill.) that can be used to control spontaneous bleeding and/or treat hemophilia A/B patients. The FEIBA VH mixture includes Factors II, IX, and X (mainly non-activated), Factor VII (mainly activated), and Factor VIII:C (about 1 to 6 units/ml). The FEIBA VH mixture benefits from the use of counter pressure in that the protein mixture can be filtered at relatively high filtration rates with little to no loss in protein activity when counter pressure is applied.

The liquid mixture containing the protein and the dispersed contaminant is then purified by passing the liquid mixture through a filter. Filters suitable for use according to the disclosed method are not particularly limited and can include surface filters, for example dead-end filters (i.e., in which the fluid to be filtered perpendicularly approaches the filter surface) and cross-flow filters (i.e., in which the fluid to be filtered travels parallel to the filter surface). See, e.g., *Kirk-Othmer Encyclopedia of Chemical Technology*, vol. 10, pp. 788-853 ("Filtration") ($4^{th}$ ed., 1993). The filters also are not particularly limited with respect to their classification size (i.e., the size above which dispersed material is retained on the filter and the size below which dispersed material passes into the filtrate). Once a filter classification size is selected for a particular application (i.e., dispersed material to be retained vs. dispersed material to pass into the filtrate), the filter should be operated considering the amount of shear generated by the carrier liquid flowing through the filter relative to the shear sensitivity of the particular protein being filtered.

A preferred filter medium is a porous membrane, which is generally available in various sizes (i.e., filter surface area; for example ranging from about $0.001 \text{ m}^2$ to about $5 \text{ m}^2$) and configurations (e.g., filter discs, filter cartridges). The porous membrane can be formed from materials such as cellulose nitrate, cellulose acetate, vinyl polymers, polyamides, fluorocarbons, and polyethersulfones. The porous membrane includes pores generally having a highly uniform size that is selected depending on the size of the dispersed contaminant to be removed from the liquid mixture. For example, in sterile filtration operations intended to remove microorganisms (while allowing the protein to pass through the filter membrane into the filtrate), the pores preferably have a size in a range of about 0.1 µm to about 0.5 µm, or about 0.15 µm to about 0.25 µm, for example about 0.2 µm or about 0.22 µm. Suitable porous membrane filters can also include both a 0.2 µm/0.22 µm filter and a coarser (e.g., about 0.45 µm) prefilter to improve throughput and limit cake accumulation at the 0.2 µm/0.22 µm filter surface. Examples of suitable commercial porous membrane filters for the sterile filtration of liquid mixtures with proteins include a SARTOBRAN P 0.2 µm cellulose acetate membrane (including both 0.2 µm filtration pores and a prefilter membrane having 0.45 µm filtration pores; available from Sartorius AG, Göttingen, Germany) and a SUPOR EKV 0.2 µm polyethersulfone membrane (available from Pall Corporation, East Hills, N.Y.).

FIG. 1 illustrates the flow of the liquid mixture through a filter apparatus 100, for example a cartridge filter having a porous membrane. As illustrated, the liquid mixture enters the sealed filter apparatus 100 via an inlet 110 into an inlet chamber 120. The fluid in the inlet chamber 120 is pressurized, having a first pressure $P_1$ that is generally above ambient pressure (i.e., about 1 bar absolute). The first pressure $P_1$ in the inlet chamber 120 drives the carrier liquid and the protein in the liquid mixture through a porous filter membrane 130. The material passing through the filter membrane 130 forms a filtrate including both the carrier liquid and the protein in a filtrate chamber 140. The fluid in the filtrate chamber 140 is also pressurized, having a second pressure $P_2$ that is less than the first pressure $P_1$, but which is generally above ambient pressure. The purified filtrate then exits the filter apparatus 100 via an outlet 150. The flow rate through the outlet 150 (and the second pressure $P_2$) is regulated via a counter pressure regulator 160.

The pores of the filter membrane 130 are sized to remove at least of the portion of the dispersed contaminants contained in the liquid mixture, retaining the removed dispersed contaminants on the inlet-side of the filter membrane 130 (i.e., in the inlet chamber 120). Preferably, the filter membrane 130 is sized to remove substantially all of the dispersed contaminants initially contained in the inlet liquid mixture; thus, the filtrate is substantially free (or free) of the dispersed contaminants. Specifically, the filtrate should not contain the dispersed contaminants in an amount that would adversely affect the use of the filtered and purified protein mixture as a therapeutic composition. For example, when the dispersed contaminants include microorganisms, the filter membrane 130 should be able to remove at least about $10^7$ colony forming units per $cm^2$ of filter area.

The first pressure $P_1$ of the inlet liquid mixture can be applied by any suitable source, for example gravity, a compressed gas (e.g., compressed air), or a pump (e.g., a low-shear pump). Preferably, the first pressure $P_1$ is at least about 200 mbar gauge, or in a range of about 200 mbar gauge to about 1,000 mbar gauge (i.e., about 1 bar gauge), for example about 300 mbar gauge. Counter pressure (or back pressure) also can be applied by any suitable source, for example a conventional valve (illustrated in FIG. 1 as the counter pressure regulator 160), to obtain the second pressure $P_2$ of the outlet filtrate. Additionally, the counter pressure also can be applied by a flow constriction, obstruction, etc. along the length of the outlet 150 path. As a result of the first and second pressures $P_1$ and $P_2$, the applied counter pressure generates a (positive) pressure differential $P_1-P_2$ to drive the carrier liquid and the protein through the filter and into the filtrate. The pressure differential is low, with suitable maximum pressure differentials depending of a variety of factors, for example the particular protein being filtered and the particular filter being used. In particular, the pressure differential is preferably not more than about 300 mbar, 200 mbar, 150 mbar, or 120 mbar, more preferably not more than about 90 mbar or 50 mbar, even more preferably not more than about 20 mbar or 10 mbar, for example not more than about 5 mbar or not more than about 3 mbar.

At such differential pressures, the flow rate across the filter is low enough to generate a low-shear environment that does not substantially damage, destroy, or reduce the activity of the protein. The low-shear environment further does not substantially limit the yield of the filtration process.

Specifically, it has been observed that a low differential pressure can be used to obtain both a relatively high and a substantially constant filtration rate. In particular, a low differential pressure can be applied to obtain an average filtration flow rate of at least about 300 g/min·m$^2$, for example about 300 g/min·m$^2$ to about 1000 g/min·m$^2$ or about 400 g/min·m$^2$ to about 800 g/min·m$^2$, where the units are mass of filtrate (i.e., grams carrier liquid and protein combined) obtained per unit time (i.e., minutes) and normalized per unit surface area of the filter (i.e., m$^2$). The low differential pressure resulting from the application of counter pressure also can generate a substantially constant filtration rate, in particular after completion of a start-up transient, thus improving the net capacity of a filter. In contrast to the observed filtration rate at a low differential pressure (and in contrast to general filtration theory, which implies that the filtration rate is proportional to the differential pressure across the filter), a higher differential pressure (e.g., above about 100 mbar) tends to decrease the rate of filtration. Thus, conventional filtration methods, which apply differential pressures of at least about 100 mbar to at least about 300 mbar, are unable to attain the average filtration flow rates observed in the disclosed method.

Further, it has been observed that a low differential pressure can be used to obtain a high recovery of the protein. Specifically, substantially all of the protein that is initially present in the liquid mixture is preferably recovered in the filtrate. For example, when a first concentration $C_1$ represents the concentration of the protein relative to the carrier liquid in the initial liquid mixture, and a second concentration $C_2$ represents the concentration of the protein relative to the carrier liquid in the final filtrate, then a recovery ratio $C_2/C_1$ of the disclosed filtration method is preferably at least about 0.95, and more preferably at least about 0.99.

The disclosed method of counter-pressure filtration is useful when applied to proteins because the method provides accurate control of the filtration flow rate. Pressure sources that are used to drive the liquid mixture through the filter generally provide an excessive pressure that results in high shear rates, which, in turn, lead to filter plugging and protein damage. It is generally difficult, if not impossible, to regulate a single pressure source relative to the ambient pressure such that the resulting differential pressure is both low enough and sufficiently constant to result in an average flow rate through the filter that is sufficiently low to avoid protein damage and substantially constant. By applying counter pressure to the filtrate-side of the process fluid, however, a relatively high pressure source (i.e., the first pressure $P_1$) can be accurately counter balanced (i.e., with the second pressure $P_2$) to obtain a low and substantially constant pressure differential (i.e., $P_1-P_2$).

EXAMPLES

The following examples are provided for illustration and are not intended to limit the scope of the invention.

Examples 1-8

An aqueous liquid mixture of the shear-sensitive, blood coagulation cascade protein vWF was sterile filtered to determine the effect of pressure (and counter pressure) and other process variables (e.g., filter size and type) on filtration efficacy, for example based on the recovered activity of vWF in the filtrate, the average flow rate of the filtrate, and the ability to scale up the process.

An aqueous liquid mixture of recombinant vWF ("rVWF:Rco") having an activity of 125 IU/ml and concentration of 1159 µg/ml (bicinchoninic acid ("BCA") assay) of was prepared for use in each of the following Examples 1-8. Low-molecular-weight salts were added to adjust the pH and osmolarity of the mixture to values of 7.3 and about 400 mOsmol/l (milliosmoles/liter), respectively. Because Examples 1-8 were intended to isolate the fluid dynamic effects (e.g., shear) on the protein in the neighborhood of a filter, no other dispersed contaminants or materials (e.g., bacteria, other microorganisms, or other proteins) were added to the mixture. The components of the aqueous liquid mixture are summarized in Table 1.

TABLE 1

Liquid Mixture Composition for Examples 1-8

| Mixture Component | Concentration |
|---|---|
| rVWF:Rco | 125 IU/ml |
| Protein (BCA) | 1159 μg/ml |
| Sodium Citrate Dihydrate | 4.53 g/l |
| Glycin | 1.16 g/l |
| Trehalose | 10.26 g/l |
| Mannitol | 20.52 g/l |
| Polysorbate 80 (10:1 stock dilution) | 1.03 g/l |
| Water-For-Injection (WFI) | Balance |

The aqueous liquid mixture was then tested in the following manner. A test volume of at least about 500 ml of the mixture was added to a pressure-resistant stainless steel vessel. The outlet of the vessel was connected to the inlet of a (steam-sterilized) sterile filter with a first section of silicone tubing. A second section of silicone tubing with a length of about 10 cm was attached to the outlet of the sterile filter housing. The filtrate effluent from the sterile filter was collected in a beaker placed on a balance to monitor the filtration rate. The balance was interfaced with a computer to record at set intervals the total amount of filtrate collected as a function of time.

In Examples 1-7, a SARTOBRAN P 0.2 μm cellulose acetate membrane filter (including a 0.45 μm prefilter) was used. In Example 8, a SUPOR EKV 0.2 μm polyethersulfone membrane filter was used. Examples 1-3 used disc membrane filters, while Examples 4-8 used cartridge membrane filters. The filter surface area of each filter is provided in Table 2.

For each of Examples 1-8, the test volume of the aqueous liquid mixture was filtered at constant pressure. In Example 1, the aqueous liquid mixture entering the sterile filter had an applied pressure of about 100 mbar gauge (i.e., about 1.1 bar absolute), based on the height of the column of fluid feeding the sterile filter from the stainless steel vessel. In Examples 2-8, clean compressed air was use to provide the pressure of the aqueous liquid mixture entering the sterile filter, which pressure ranged from 150 mbar to 300 mbar, as indicated in Table 2. In Examples 1-4, counter-pressure filtration was not performed (i.e., the outlet tube of the sterile filter was open to the atmosphere as the filtrate emptied into the collection beaker); thus, the pressure differential driving the filtration was essentially the pressure of the aqueous liquid mixture entering sterile filter. For Examples 5-8, counter pressure was applied to the filtrate by attaching and tightening a clamp to the outlet tube of the sterile filter. The pressure differential for Examples 5-8 (indicated in Table 2) was estimated based on the average filtrate flow rate measured during the filtration and the known pressure drop-flow rate characteristics of the commercial filters used.

Generally, in each example, the mixture was filtered shortly after the aqueous liquid mixture test volume was prepared. However, in Example 5, the mixture was filtered after an eight-hour delay to examine any potential effect of storage on the disclosed method.

Table 2 summarizes the test parameters for each of Examples 1-8.

TABLE 2

Filtration Test Parameters for Examples 1-8

| | Example: | | | | | | | |
|---|---|---|---|---|---|---|---|---|
| | 1 | 2 | 3 | 4 | 5 | 6 | 7 | 8 |
| Filter | | | | | | | | |
| Membrane Configuration | Disc | Disc | Disc | Cart. | Cart. | Cart. | Cart. | Cart. |
| Surface Area (m$^2$) | 0.0017 | 0.0017 | 0.0017 | 0.015 | 0.015 | 0.015 | 0.03 | 0.022 |
| Pore Size (μm) | 0.45/0.2 | 0.45/0.2 | 0.45/0.2 | 0.45/0.2 | 0.45/0.2 | 0.45/0.2 | 0.45/0.2 | 0.2 |
| Pressure | | | | | | | | |
| Counter Pressure | No | No | No | No | Yes | Yes | Yes | Yes |
| Applied P$_1$ (mbar gauge) | 100 | 200 | 300 | 150 | 300 | 300 | 300 | 300 |
| Differential P$_1$ – P$_2$ (mbar) | 100 | 200 | 300 | 150 | 2.6 | 3.2 | 3.5 | 3.8 |

The results of the filtration tests are summarized in Table 3. In Table 3, the "filtrate amount" represents the mass of filtrate (i.e., including water and any recovered vWF) obtained during the individual test. For Examples 1-4, the filtration test was performed until the filter became plugged and substantial amounts of filtrate could no longer be obtained. For Examples 5-8, the filtration test was performed until several hundreds of grams of filtrate were obtained, and the test was terminated while the filter was unplugged and still capable of further filtration. The "filter capacity" entry in Table 3 represent the filtrate amount normalized per unit area of filter surface. The ">" for Examples 5-8 indicates that the filter capacity is a lower estimate of the actual capacity, inasmuch as the filter did not become plugged during the test. The "average flow rate" entry in Table 3 represents the filtrate amount averaged over the course of the test and normalized per unit area of filter surface.

TABLE 3

Filtration Results for Examples 1-8

| | Example: | | | | | | | |
|---|---|---|---|---|---|---|---|---|
| | 1 | 2 | 3 | 4 | 5 | 6 | 7 | 8 |
| Filtrate Amount (g) | 27 | 5.4 | 5.1 | 75 | 390 | 720 | 1080 | 550 |
| Filter Capacity (kg/m$^2$) | 16 | 3.2 | 3.0 | 5.0 | >26 | >48 | >36 | >25 |
| Avg. FlowRate Rate (g/min · m$^2$) | 290 | 148 | 72 | 53 | 330 | 410 | 450 | 760 |

From Table 3, it is apparent that the counter-pressure filtration of proteins significantly increases filtration capacity and flow rate. At even moderately low applied pressures ranging from 100 mbar to 300 mbar for vWF and the utilized filters (where the utilized filter cartridges can withstand maximum pressures ranging from about 2 bar to about 5.5 bar), Examples 1-4 indicate that filter capacity is low and rapidly decreases with increasing pressure. In contrast, when a counter pressure is applied to the filtrate to reduce the pressure differential, Examples 5-8 exhibit substantially larger filtration capacities and flow rates. This observed behavior is unexpected, inasmuch as filters are generally characterized by a direct proportionality between the filtration flow rate and pressure differential:

$$\frac{Q}{A} = \frac{\Delta p}{\mu R} \qquad \text{Eqn. (1)}$$

In Equation (1), Q is the filtration flow rate (volume or mass per unit time), A is the filter surface area, Δp is the pressure differential across the filter, μ is the viscosity of the fluid being filtered, and R is an empirical resistance of the filter medium. The similarity among the results of Examples 5-8 further indicates that the benefits of counter-pressure filtration can be obtained using variable filter media and/or filter sizes.

The time-dependent filtration data (i.e., filtrate collected as a function of time) for Examples 4 and 6 are shown in FIG. 2. From FIG. 2, it is apparent that the higher pressure differential for Example 4 results in a relatively high filtration rate over the first 10-15 minutes of the filtration test. However, the higher pressure differential in Example 4 also results in a more rapid plugging of the filter. In contrast, the use of counter pressure in Example 6 lowers the pressure differential and the initial filtration rate. Specifically, after the initial transient period of about 10 minutes to about 15 minutes, the low pressure differential creates a low-shear filtration environment that prevents the filter from becoming plugged by vWF, thereby increasing the filter capacity and filtration flow rate over the life of the filter, and further resulting in a filtration flow rate that is substantially constant.

As summarized in Table 4, the filtrate of each of Examples 1-3 and 5 was also analyzed to measure the level of recombinant vWF in the filtrate to determine whether the filtration process adversely affected the concentration of the recombinant vWF present in the initial aqueous liquid mixture. In the absence of counter pressure, Examples 1-3 indicate that even moderately low pressure differentials can damage or destroy proteins during filtration, with up to about half of the recombinant vWF being lost during filtration at pressure differentials of 200 mbar and 300 mbar. This filtration loss is avoided by the use of counter pressure, as shown in Example 5, where no measurable reduction in the rVWF:Rco concentration occurred and only a 4% decrease in the measured protein (BCA) content occurred. Thus, substantially all of the protein that is initially present in the aqueous liquid mixture can be recovered in the filtrate.

TABLE 4

Recovery of vWF in the Filtrate

| | | Example: | | | |
|---|---|---|---|---|---|
| | Stock | 1 | 2 | 3 | 5 |
| rVWF:Rco (IU/ml) | 125 | n/a | 69 | 69 | 126 |
| Protein (BCA) (μg/ml) | 1159 | 1054 | 724 | 715 | 1113 |

Examples 9-20

Aqueous solutions containing Factor VIII were tested on SARTOBRAN® filters, with a SARTOCLEAN pre-filter, to determine the effect of counter-pressure on filtration efficacy, for example, based on the filter surface area required. In Examples 9-13, counter-pressure filtration was not performed; the initial applied pressure was 100 mbar to 500 mbar. In Examples 14-16, the pressure differential was 200 mbar, and in Examples 17-20, the pressure differential was reduced to less than 150 mbar. The surface area of each filter was 1.2 m$^2$. Table 5 contains the Factor VIII activity before and after filtration and yield for each experiment.

TABLE 5

Recovery of FVIII in the Filtrate

| | Example: | | | | | | | | | | | |
|---|---|---|---|---|---|---|---|---|---|---|---|---|
| | 9 | 10 | 11 | 12 | 13 | 14 | 15 | 16 | 17 | 18 | 19 | 20 |
| | Dead end filtration | | | | | | | Counter-pressure filtration | | | | |
| Starting volume (ml) | 695 | 670 | 710 | 623 | 698 | 702 | 684 | 727 | 717 | 650 | 707 | 704 |
| Filtrate volume (ml) | 685 | 667 | 696 | 617 | 687 | 696 | 667 | 719 | 708 | 640 | 701 | 698 |
| Number of filters | 10 | 10 | 15 | 5 | 15 | 7 | 10 | 8 | 5 | 5 | 6 | 5 |
| Total filter area (m$^2$) | 12 | 12 | 18 | 6 | 18 | 8.4 | 12 | 9.6 | 6 | 6 | 7.2 | 6 |
| Activity before filtration (IU/ml) | 11.5 | 11.8 | 14.5 | 8.04 | 8.41 | 13.7 | 7.99 | 12.2 | 10 | 9.46 | 9.74 | 8.95 |
| Activity after filtration (IU/ml) | 11.2 | 12.1 | 12.7 | 9.94 | 10.6 | 13.3 | 8.63 | 11.1 | 13.8 | 13 | 13.5 | 12.2 |

TABLE 5-continued

Recovery of FVIII in the Filtrate

| | Example: | | | | | | | | | | | |
|---|---|---|---|---|---|---|---|---|---|---|---|---|
| | 9 | 10 | 11 | 12 | 13 | 14 | 15 | 16 | 17 | 18 | 19 | 20 |
| | | Dead end filtration | | | | | | Counter-pressure filtration | | | | |
| Activity Yield (%) | 96 | 102 | 86 | 122 | 124 | 96 | 105 | 90 | 136 | 135 | 137 | 135 |
| Filter capacity (kg/m²) | 57.9 | 55.8 | 39.4 | 103.8 | 38.8 | 83.6 | 57 | 75.7 | 119.5 | 108.3 | 98.2 | 117.3 |
| Average Activity Yield | | | 106 | | | | | | | 119 | | |

The preceding data demonstrates that far less filter area is required when counter-pressure filtration is employed for the same amount of active substance. Counter-pressure filtration stabilizes the filtration, and when differential pressure is optimized, the average activity yield is improved.

Examples 21-25

Solutions containing Factor XIII were tested on a PALL® POSIDYNE® N66 nylon filter to determine the effect of counter-pressure on filtration efficacy, for example, based on the recovered activity and protein concentration of Factor XIII in the filtrate. The filter area was 0.82 m². In Examples 21-23, counter-pressure filtration was not performed; the applied pressure for these examples was 600 mbar. In Examples 24-26, the pressure differential was about 100 mbar. Table 6 contains the protein concentration and activity before and after filtration and yield for each experiment.

TABLE 6

Recovery of FXIII in the Filtrate

| | Example: | | | | | |
|---|---|---|---|---|---|---|
| | 21 | 22 | 23 | 24 | 25 | 26 |
| | | Dead end filtration | | | Counter-pressure filtration | |
| Activity before filtration (IU/ml) | 217.9 | 188 | 161.7 | 158 | 187.2 | 118.8 |
| Activity after filtration (IU/ml) | 194.6 | 179.8 | 180.2 | 189.4 | 184.8 | 115.2 |
| Activity Yield (%) | 89 | 96 | 111 | 120 | 99 | 97 |
| Average Activity Yield | | 99 | | | 105 | |
| Protein before filtration (μg/ml) | 4.65 | 5.57 | 6.28 | 5.9 | 5.66 | 3.66 |
| Protein after filtration (μg/ml) | 3.59 | 4.48 | 5.04 | 5.03 | 5.25 | 3.73 |
| Protein Yield (%) | 77 | 80 | 80 | 85 | 93 | 102 |
| Average Protein Yield | | 79 | | | 93 | |

As shown in Table 6, activity yield and protein yield are substantially improved with the use of counter-pressure during filtration.

The foregoing description is given for clearness of understanding only, and no unnecessary limitations should be understood therefrom, as modifications within the scope of the invention may be apparent to those having ordinary skill in the art.

Throughout the specification, where compositions are described as including components or materials, it is contemplated that the compositions can also consist essentially of, or consist of, any combination of the recited components or materials, unless described otherwise.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

What is claimed is:

1. A method of filtering a liquid protein mixture, the method comprising:
   providing a liquid mixture at a first pressure ($P_1$), the liquid mixture comprising a carrier liquid, a protein at a first concentration ($C_1$) relative to the carrier liquid, and a dispersed contaminant;
   passing the liquid mixture through a filter to form a filtrate at a second pressure ($P_2$), the filtrate comprising the carrier liquid and the protein at a second concentration ($C_2$) relative to the carrier liquid, wherein $P_1$ is greater than ambient pressure and less than about 1 bar gauge, $P_2$ is greater than ambient pressure and less than $P_1$, and the filter is sized to remove at least a portion of the dispersed contaminant from the liquid mixture; and,
   applying a counter pressure to the filtrate to ensure that a pressure differential between the first and second pressures ($P_1-P_2$) is not more than about 300 mbar, wherein at least about 85% of the protein present in the liquid mixture is recovered in the filtrate.

2. The method of claim 1, wherein the pressure differential is not more than about 90 mbar.

3. The method of claim 1, wherein at least about 95% of the protein present in the liquid mixture is recovered in the filtrate.

4. The method of claim 3, wherein at least about 99% of the protein present in the liquid mixture is recovered in the filtrate.

5. The method of claim 1, wherein the first pressure ($P_1$) is at least about 200 mbar gauge.

6. The method of claim 1, wherein the carrier liquid comprises water.

7. The method of claim 1, wherein the dispersed contaminant comprises a microorganism.

8. The method of claim 1, wherein the filtrate is substantially free of the dispersed contaminant.

9. The method of claim 1, wherein the filter comprises a porous membrane, the porous membrane comprising pores sized from about 0.1 μm to about 0.5 μm.

10. The method of claim 9, wherein the pores are sized at about 0.2 μm or about 0.22 μm.

11. A method of filtering a liquid protein mixture, the method comprising:
provides a liquid mixture at a first pressure ($P_1$), the liquid mixture comprising a carrier liquid, a protein at a first concentration ($C_1$) relative to the carrier liquid, and a dispersed contaminant;
passing the liquid mixture through a filter to form a filtrate at a second pressure ($P_2$), the filtrate comprising the carrier liquid and the protein at a second concentration ($C_2$) relative to the carrier liquid, wherein $P_1$ is greater than ambient pressure and less than about 1 bar gauge, $P_2$ is greater than ambient pressure and less than $P_1$ and the filter is sized to remove at least a portion of the dispersed contaminant from the liquid mixture; and,
applying a counter pressure to the filtrate sufficient to yield an average filtrate flow rate of at least about 300 g/min·m² of filter surface area, wherein at least about 85% of the protein present in the liquid mixture is recovered in the filtrate.

12. The method of claim 11, wherein at least about 95% of the protein present in the liquid mixture is recovered in the filtrate.

13. The method of claim 12, wherein at least about 99% of the protein present in the liquid mixture is recovered in the filtrate.

14. The method of claim 11, wherein the carrier liquid comprises water.

15. The method of claim 11, wherein the dispersed contaminant comprises a microorganism.

16. The method of claim 11, wherein the filtrate is substantially free of the dispersed contaminant.

17. The method of claim 11, wherein the filter comprises a porous membrane, the porous membrane comprising pores sized from about 0.1 μm to about 0.5 μm.

18. The method of claim 17, wherein the pores are sized at about 0.2 μm or about 0.22 μm.

19. A method of filtering a liquid protein mixture, the method comprising:
providing a liquid mixture at a first pressure ($P_1$), the liquid mixture comprising a carrier liquid, a protein at a first concentration ($C_1$) relative to the carrier liquid, and a dispersed contaminant;
passing the liquid mixture through a filter to form a filtrate at a second pressure ($P_2$), the filtrate comprising the carrier liquid and the protein at a second concentration ($C_2$) relative to the carrier liquid, wherein $P_1$ is greater than ambient pressure and less than about 1 bar gauge, $P_2$ is greater than ambient pressure and less than $P_1$, and the filter is sized to remove at least a portion of the dispersed contaminant from the liquid mixture; and,
applying a counter pressure to the filtrate to ensure that a pressure differential between the first and second pressures ($P_1-P_2$) is not more than about 300 mbar and to yield an average filtrate flow rate of at least about 300 g/min·m² of filter surface area, wherein at least about 85% of the protein present in the liquid mixture is recovered in the filtrate.

20. The method of claim 19, wherein the protein comprises a blood coagulation factor.

21. The method of claim 20, wherein the blood coagulation factor is von Willebrand factor (vWF).

22. The method of claim 20, wherein the blood coagulation factor is Factor VIII.

23. The method of claim 20, wherein at least 90% of the activity of the blood coagulation factor present in the liquid mixture is recovered in the filtrate.

* * * * *